United States Patent
Brengartner et al.

(10) Patent No.: US 10,429,286 B2
(45) Date of Patent: Oct. 1, 2019

(54) VIBRONIC SENSOR

(71) Applicant: Endress + Hauser GmbH + Co. KG, Maulburg (DE)

(72) Inventors: Tobias Brengartner, Emmendingen (DE); Sascha D'Angelico, Rummingen (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 155 days.

(21) Appl. No.: 15/535,088

(22) PCT Filed: Nov. 9, 2015

(86) PCT No.: PCT/EP2015/076022
§ 371 (c)(1),
(2) Date: Jun. 12, 2017

(87) PCT Pub. No.: WO2016/096242
PCT Pub. Date: Jun. 23, 2016

(65) Prior Publication Data
US 2017/0343459 A1    Nov. 30, 2017

(30) Foreign Application Priority Data
Dec. 18, 2014   (DE) .......................... 10 2014 119 061

(51) Int. Cl.
*G01N 11/16*    (2006.01)
*G01N 29/02*    (2006.01)
(Continued)

(52) U.S. Cl.
CPC .............. *G01N 11/16* (2013.01); *G01F 1/20* (2013.01); *G01F 23/0069* (2013.01);
(Continued)

(58) Field of Classification Search
CPC ........ G01N 11/16; G01N 11/06; G01N 11/10; G01N 29/022; G01N 29/036; G01N 9/002;
(Continued)

(56) References Cited

U.S. PATENT DOCUMENTS

| | | | | |
|---|---|---|---|---|
| 4,896,318 A | * | 1/1990 | Kokubo | ................. H04B 3/232 370/289 |
| 5,452,611 A | * | 9/1995 | Jones | .................. G01F 23/2961 73/1.73 |

(Continued)

FOREIGN PATENT DOCUMENTS

| | | |
|---|---|---|
| CN | 1602411 A | 3/2005 |
| CN | 101517381 A | 8/2009 |

(Continued)

OTHER PUBLICATIONS

German Search Report, German Patent Office, Munich, DE—dated Oct. 5, 2015.

(Continued)

*Primary Examiner* — Helen C Kwok
(74) *Attorney, Agent, or Firm* — Bacon & Thomas, PLLC

(57) ABSTRACT

A vibronic sensor for determining and/or monitoring at least one process variable of a medium in a container. The sensor at least comprising: a unit which can oscillate mechanically; a driving/receiving unit; and an electronic unit. The driving/receiving unit is designed to excite, by an electrical excitation signal, mechanical oscillations in the unit which can oscillate mechanically and is designed to receive the mechanical oscillations of the unit which can oscillate mechanically, and to convert the mechanical oscillations into an electrical receiving signal. The electronic unit is designed to generate the excitation signal on the basis of the receiving signal and to determine that at least one process variable from the receiving unit. The electronic unit com- (Continued)

prises at least one adaptive filter; and the electronic unit is designed to set the filter characteristic of the adaptive filter in such a way that there is a target phase shift between the excitation signal and the receiving signal.

18 Claims, 2 Drawing Sheets

(51) Int. Cl.
  *G01N 29/036*  (2006.01)
  *G01F 23/296*  (2006.01)
  *G01F 1/20*  (2006.01)
  *G01F 23/00*  (2006.01)
  *G01N 9/00*  (2006.01)
  *G01H 11/06*  (2006.01)

(52) U.S. Cl.
  CPC ......... *G01F 23/2967* (2013.01); *G01H 11/06* (2013.01); *G01N 9/002* (2013.01); *G01N 29/022* (2013.01); *G01N 29/036* (2013.01); *G01N 2009/006* (2013.01); *G01N 2291/012* (2013.01); *G01N 2291/02818* (2013.01); *G01N 2291/02836* (2013.01); *G01N 2291/0427* (2013.01)

(58) Field of Classification Search
  CPC .... G01F 1/20; G01F 23/2967; G01F 23/0069; G01F 23/2965
  See application file for complete search history.

(56) References Cited

U.S. PATENT DOCUMENTS

| | | | | |
|---|---|---|---|---|
| 6,378,364 B1* | 4/2002 | Pelletier | ................... | E21B 47/06 73/152.47 |
| 6,389,891 B1* | 5/2002 | D'Angelico | ........ | G01F 23/2961 73/290 V |
| 2005/0210954 A1* | 9/2005 | Raffalt | ................ | G01F 23/2967 73/1.82 |
| 2006/0131994 A1* | 6/2006 | D'Angelico | ........ | G01F 23/2967 310/317 |
| 2007/0186684 A1* | 8/2007 | Pham | .................... | G01F 1/8409 73/861.357 |
| 2009/0205411 A1* | 8/2009 | Muller | ................ | G01F 23/2967 73/64.53 |
| 2010/0083750 A1* | 4/2010 | D'Angelico | ........ | G01F 23/2967 73/290 V |
| 2010/0083752 A1* | 4/2010 | Malinek | ................ | G01F 23/296 73/32 R |
| 2012/0119758 A1* | 5/2012 | Urban | ................. | G01F 23/2965 324/617 |
| 2012/0279283 A1* | 11/2012 | Brengartner | ........ | G01F 23/2961 73/54.41 |
| 2013/0036816 A1* | 2/2013 | Urban | ................... | G01F 23/296 73/32 A |
| 2013/0139585 A1* | 6/2013 | D'Angelico | ........ | G01F 23/2966 73/290 V |
| 2014/0245834 A1* | 9/2014 | Urban | ................. | G01F 23/2965 73/584 |
| 2014/0373607 A1* | 12/2014 | Bauer | .................... | G01N 9/002 73/64.53 |
| 2015/0135826 A1* | 5/2015 | Muller | ................ | G01F 23/2966 73/290 V |
| 2016/0059153 A1* | 3/2016 | Smith | .................. | B01D 21/245 210/744 |
| 2016/0109285 A1* | 4/2016 | Brengartner | ........ | G01F 23/0069 702/56 |
| 2018/0024097 A1* | 1/2018 | D'Angelico | ........... | G01N 9/002 73/32 A |
| 2018/0031460 A1* | 2/2018 | Brengartner | ........... | G01N 11/16 |

FOREIGN PATENT DOCUMENTS

| | | |
|---|---|---|
| CN | 103080706 A | 5/2013 |
| CN | 103608651 A | 2/2014 |
| DE | 19530393 A1 | 2/1997 |
| DE | 10161071 A1 | 6/2003 |
| DE | 102006034105 A1 | 1/2008 |
| DE | 102010028303 A1 | 12/2011 |
| DE | 102010040219 A1 | 3/2012 |
| DE | 102011075113 A1 | 11/2012 |
| DE | 102012101667 A1 | 8/2013 |
| DE | 102014119061 A1 | 6/2016 |
| EP | 0320637 A2 | 6/1989 |

OTHER PUBLICATIONS

International Search Report, EPO, The Netherlands—dated Feb. 2, 2016.
English Translation of the International Preliminary Report on Patentability, WIPO, Geneva, CH—dated Jun. 29, 2017.
Chinese Office Action in corresponding Chinese Application No. 201580067923.1, dated Dec. 25, 2018.

* cited by examiner

VIBRONIC SENSOR

TECHNICAL FIELD

The invention relates to a vibronic sensor for determining and/or monitoring at least one process variable of a medium, and a method for operating the vibronic sensor.

BACKGROUND DISCUSSION

Vibronic sensors are often used in process and/or automation technology. In the case of fill-level measuring devices, they have at least one mechanical oscillating unit—for example, a vibrating fork, a rod, or a membrane. During operation, the latter is excited into mechanical oscillation by a driving/receiving unit, often in the form of an electromechanical transducer that can, in turn, be a piezoelectric drive—for example, or an electromagnetic drive. The mechanical oscillating unit can, however, also be designed as an oscillating pipe in the case of flow meters, through which the respective medium flows, such as in a measuring device operating under the Coriolis principle.

A wide variety of corresponding field devices are made by the applicant and, in the case of fill-level measuring devices, are distributed under the name LIQUIPHANT or SOLIPHANT. The underlying measurement principles are known in principle from numerous publications. The driving/receiving unit excites the mechanically oscillating unit to mechanical oscillation via an electrical excitation signal. Conversely, the driving/receiving unit can receive the mechanical oscillations of the mechanical oscillating unit and transform them into an electrical receiving signal. The driving/receiving unit is accordingly either a separate driving unit and a separate receiving unit, or a combination driving/receiving unit.

Both the excitation signal and the receiving signal are characterized by their frequency, amplitude, and/or phase. Changes in these variables are, therefore, usually used for determination of the appropriate process variables, such as a pre-determined fill-level of a medium in a container or the density and/or viscosity of a medium, or the flow of a medium through a pipe. In the case of a vibronic limit level switch for liquids, for example, a distinction is made as to whether the oscillating unit is covered with the fluid or vibrates freely. The two states, the free state and the covered state, are thus differentiated—for example, based upon different resonant frequencies, i.e., a frequency shift. The density and/or viscosity, in turn, can be gauged using such a measuring device only if the oscillating unit is covered by the medium.

The driving/receiving unit is usually part of a feedback electrical oscillation circuit by which the excitation of the mechanical oscillating unit to mechanical oscillations is accomplished. A specifiable value for the excitation is frequently set via a control circuit for the phase shift, i.e., a target value for the phase shift between the excitation signal and the receiving signal. For example, an amplification factor of $\geq 1$ and oscillating circuit conditions according to which all phases occurring in the oscillating circuit result in a multiple of 360° must be met for a resonant oscillation. A variety of methods for stimulating a mechanically oscillating unit or for setting a specifiable phase shift are known from the prior art. A basic distinction can be made here between an analog and a digital excitation, wherein the difference is between the oscillating circuit, made up of analog components that must be adapted to the type of sensor used, and digital methods, which are, in principle, universally applicable.

According to a frequently used excitation principle, the control circuit includes an amplifier and a phase shifter, by means of which the receiving signal is coupled back to the transmission signal in order to set the specifiable value for the phase shift between the excitation signal and the receiving signal. According to German patent, DE102006034105A1, for example, an adjustable phase shifter is used. The phase shifter is controlled via a control unit that measures the frequency of the previously amplified receiving signal and is at least based upon stored data on the frequency phase dependence of an amplifier unit.

An amplifier is also known from German patent, DE102007013557A1 that has an adjustable amplification factor, which is set by a control unit in such a manner that the amplitude of the transmission signal is generally located within a specifiable amplitude band.

A vibronic sensor is known from German patent, DE102005015547A1, wherein the electronics unit is provided with at least one all-pass filter for setting a target value for the phase shift. The all-pass filter changes the phase of an electrical signal at a constant gain as a function of the frequency. The all-pass filter can especially be controlled or regulated in such a manner that the phase between the excitation signal and the receiving signal is adjustable. According to one embodiment of the invention, the receiving signal is preferably only filtered and/or amplified before it is supplied to the all-pass filter, processed by it, and returned.

In the case of an analog excitation, however, the analog components, from which the oscillation circuit is built, must necessarily be adapted to the type of sensor used. The robustness of the sensor, especially with regard to external vibrations, is further dependent upon the selectivity of the filter used in each case for signal processing or evaluation, wherein the filters used determine the phase response of the electronics unit. The greater the pitch of the phase response, the narrower the frequency range to be covered by the filter is. Accordingly, there can be circumstances in which the sensor no longer oscillates in resonance.

Another excitation method is described in German patent, DE102009026685A1. The mechanically oscillating unit is successively excited to mechanical oscillations via consecutive discrete excitation frequencies by means of a so-called frequency sweep within a pre-determined frequency band in the operating range of the oscillating unit, and the corresponding receiving signals are recorded. Via the frequency sweep, that excitation frequency is determined at which the oscillating unit oscillates at an oscillating frequency that corresponds to a specifiable value for the phase shift. This excitation frequency is applied in each case to the oscillating unit. An advantageous development of this method is the subject matter of German patent, DE102009028022A1, in which the evaluation of the received signal is simplified by the receiving signal being sampled and evaluated phase-selectively only at specific instants. Similarly, it is proposed in German patent, DE102010030982A1 that the receiving signal be sampled at pre-determined discrete instants in relation to the transmission signal, the sampled voltage values of the receiving signal be each compared to the target value, which the receiving signal at this instant assumes if the specifiable value for the phase shift is present, and, in the case of deviation of the voltage value from the target value, the frequency of the transmission signal be decreased or increased based upon whether the deviation is positive or negative.

In the case of an excitation via a frequency sweep and the evaluation of the respective phases and/or amplitudes of the receiving signal, it must also be noted that there is a dependency between the flow speed of the frequency sweep and the frequency resolution.

An additional digital possibility for a vibronic sensor to regulate the phase shift between an excitation signal and a receiving signal is disclosed in DE00102010030982A1. The method described there is based upon the functional principle of a phase-locked loop, PLL. The frequency of the excitation signal is set here in such a manner that there is a specifiable value for the phase shift between the excitation signal and the receiving signal.

This type of excitation has decisive advantages with respect to evaluation speed, compared to excitation via a frequency sweep. To be sure, however, at least one phase detector is required, which influences robustness, i.e., especially, the stability of the control, among other things, if external vibrations occur, as well as the precision of the control circuit. In order for evaluation to be done in a stable manner, it must additionally be ensured that the amplitude of the excitation signal is kept at a constant value.

In order to reduce problems from the occurrence of external vibrations during the operation of a vibronic sensor, such as vibrations from pumps or ultrasonic baths, German patent, DE102012101667A1 proposes configuring a control/evaluation unit in such a way as to control the oscillation excitation in the presence of at least one external vibration as a function of the frequency and/or amplitude of the external vibrations, so that the receiving signal is essentially not disturbed by the external vibration, and/or to suppress at least one frequency of an external vibration.

SUMMARY OF THE INVENTION

Starting from the aforementioned prior art, the object of the present invention is to provide a robust vibronic sensor, as well as a method for operating the sensor.

This object is achieved according to the invention by a vibronic sensor for determining and/or monitoring at least one process variable of a medium in a container comprising at least a unit which can oscillate mechanically, a driving/receiving unit, and an electronics unit, wherein the driving/receiving unit is designed to excite, via an electrical excitation signal, mechanical oscillations in the unit which can oscillate mechanically and is designed to receive the mechanical oscillations of the unit which can oscillate mechanically and to convert them into an electrical receiving signal, wherein the electronics unit is designed to generate the excitation signal on the basis of the receiving signal and to determine the at least one process variable from the receiving signal, wherein the electronics unit comprises at least one adaptive filter, and wherein the electronics unit is designed to set the filter characteristics of the adaptive filter in such a way that there is a target phase shift between the excitation signal and the receiving signal. If the filter characteristics are appropriately set, a specific, defined target phase shift between the excitation signal and the receiving signal results. The target phase shift corresponds to a specifiable value for the phase shift between the excitation signal and the receiving signal.

The filter characteristics generally describe the behavior of the filter, i.e., its filter properties, and are determined by the so-called filter requirements, such as those for the passbands and stopbands. In some cases, the filter requirements also include specifications with regard to the group delay, maximum overshooting, edge steepness, center frequency, quality, etc. For example, one of the known filter characteristics, such as Bessel, Legendre, Butterworth, Tschebyscheff, Gauss or the like, can be used. Depending upon the filter characteristics chosen, the transfer function, by which the amplitude, phase response, and the frequency response are fully determined, is appropriately designed for the filter.

The filter characteristics of an adaptive filter can be adjusted during operation. For example, the quality of the filter that correlates to the bandwidth as well as the location of the center frequency can be adjusted. Accordingly, the phase shift $\phi_{Filter}$ between the input and output signals can be appropriately adjusted by setting an appropriate filter characteristic. As a consequence of setting the phase shift between the input and output signals of the filter to a specifiable value, the frequency is set in such a manner that there is a target phase shift of $\phi_{soll}=360°-\phi_{Filter}$ between the excitation signal and the receiving signal. A target phase shift can also be set between the excitation signal and the receiving signal via an appropriate adjustment of the filter characteristics. Because it is an adaptive filter, i.e., it can be adjusted accordingly, the quality of the filter can be increased without limiting the respective frequency range, as would be the case with a fixed filter.

Advantageously, adjustment of the target phase shift can be accomplished independently of interfering influences that might arise, such as external vibrations. The vibronic sensor according to the invention is thus particularly robust—especially, with respect to external vibrations.

In addition, the use of adaptive filters makes the corresponding field device adaptable to a plurality of applications. For example, different phase adjustment tolerances and, thus, accompanying operational speeds for adjusting the target phase shift, can be implemented, depending upon the application. According to the application, different target phase shift values can also be set so that a suitable value is present for the target phase shift depending upon the application. The solution according to the invention can also advantageously be used in digital as well as analog embodiments of the respective oscillation circuit for exciting the oscillating unit, and can easily be adapted to different sensors—especially, different oscillating units.

In an especially preferred embodiment, the electronics unit is designed to set the target phase shift by setting the center frequency of the adaptive filter. The center frequency is also varied in such a manner that there is a target phase shift between the excitation signal and the receiving signal.

In an additional, especially preferred embodiment, the electronics unit comprises a phase control unit, which controls the center frequency of the adaptive filter in such a manner that there is a specifiable value for the phase shift between an input signal and an output signal of the filter. The setting of the target phase shift between the excitation signal and the receiving signal is thus accomplished via an adjustment of the phase shift between the input signal and the output signal of the adaptive filter.

It is advantageous for the electronics unit to comprise a ring memory and/or a phase shifter, by means of which the target phase shift can be set. The setting of a specifiable value for the phase shift between an excitation signal and a receiving signal of a vibronic sensor using a ring memory and/or a phase shifter is described, for example, in German patents, DE10161071A1 and in DE10161072A1. Related to the present invention, discrete values for the receiving signal, for example, can be stored in a memory element and then transferred to the adaptive filter after an adjustable time delay. The target phase shift between the excitation signal and the receiving signal then results from two measures: from the phase shift between the excitation signal and the receiving signal of the adaptive filter set via the filter characteristics, and from the phase shift $\phi_{rs}$ produced via the ring memory and/or the phase shifter. This results in the target phase shift $\phi_{soll}$ to $\phi_{soll}=360°-\phi_{filter}-\phi_{rs}$. Advantageously, the adaptive filter can be set to its center frequency independently of the value of the target phase shift using this process. This setting corresponds to a phase shift of 0° or 90° between the input signal and the output signal of the filter. If a different value for the target phase shift between the input signal and the output signal is required that does not correspond to a value of $\phi_{soll}=360°-\phi_{filter}$, an additional appropriate phase shift must be additionally set via the ring memory and/or the phase shifter, so that the required target phase shift $\phi_{soll}=360°-\phi_{filter}-\phi_{rs}$ is set.

By setting the target phase shift, the oscillating unit executes mechanical oscillations having the appropriately corresponding frequencies. In the case of a 90° phase shift, there exists a so-called fundamental wave excitation that is a resonant oscillation in the resonant frequency—generally one which corresponds to the fundamental oscillation mode. By using an adaptive filter for exciting the oscillating unit, other phase shifts can also be set, as already mentioned. This conversion can advantageously be executed at the software level. The electronics unit and arrangement can thus be used for different phase shifts.

Advantageously, by setting the center frequency to the frequency of the excitation signal, the oscillation frequency of the mechanical oscillating unit is known. This is thus directly detected during excitation, which provides a simplification with respect to the signal evaluation within the electronics unit.

In a preferred embodiment, the bandwidth of the adaptive filter is adjustable. A high bandwidth enables simple and quick detection of the resonant frequency of the oscillating unit, because the oscillating unit can be excited in this manner using frequencies within a large frequency range. Advantageously, the oscillating circuit state can thus be implemented even within a broad frequency band.

In the case of a digital excitation based upon the principle of a phase control loop, the phase shift between the excitation signal and the receiving signal is, by contrast, controlled directly, thus requiring a controlled state of the oscillating system. The resonant frequency must therefore essentially be known. However, because the quality of the oscillating system can continuously change during operation, the search and control of the resonant frequency can be significantly more difficult when using a phase shift sweep than for the case that the present application describes. For the present invention, for example, the center frequency of the digital filter, whose quality is constant, is controlled. Furthermore, as a result of setting the target phase shift by controlling the phase shift between the input signal and the output signal of the adaptive filter, the use of at least one voltage-controlled oscillator (VCO) may be omitted.

It is again advisable to choose the smallest bandwidth possible, in order to maximize measurement precision as much as possible. Advantageously, a small bandwidth causes a significant reduction in interference.

If no resonance is detected within the maximum frequency interval detectable via the frequency sweep, a blockage, for example, and/or a defect in the mechanical oscillating unit may exist.

In a preferred embodiment, the adaptive filter is a resonator filter. In an alternate preferred embodiment, the adaptive filter is a bandpass filter—especially, a low-pass filter—especially, a second-order low-pass filter. If, for example, the center frequency of the adaptive filter is regulated to the input frequency—thus, to the frequency of the input signal of the oscillating unit—a phase shift $\phi_{filter}$ between the input and the output signals of 0° then results when using a bandpass filter. By contrast, with a second-order low-pass filter, especially one having resonance enhancement—thus, a resonator filter—a phase shift of −90° results. Depending upon the design of the sensor unit, a target phase shift between the excitation signal and the receiving signal that corresponds to a resonant excitation is then produced.

It is additionally advantageous for the phase control unit to be based upon the principle of a lock-in amplifier. A lock-in amplifier is, in principle, an extremely narrow-band bandpass filter. This approach accordingly allows for a control with an improved signal-to-noise ratio.

An advantageous embodiment provides that the target phase shift be 90°, 45°, or 0°. While a target phase shift of 90° or 0° leads to a resonant excitation of the oscillating unit as a function of the embodiment of the sensor unit, a target phase shift of 45° shows itself to be advantageous for determining density.

In an additional advantageous embodiment, at least a first and a second phase shift are alternately adjustable. It is obvious that three or more different target phase shifts can be set alternately. Thus, a pre-determined fill-level and the density of the medium can be alternately determined, for example. Similarly, the electronics unit can additionally be designed to simultaneously determine the viscosity, as well. A plurality of process variables can also be detected via the same sensor element and via the same electronics unit.

An especially preferred embodiment includes the electronics unit comprising an amplitude control unit for regulating the amplitude of the excitation signal to a specifiable value or to a value within a specifiable interval. The amplitude dynamics can advantageously be controlled via an amplitude control unit. Among other things, the damping of the oscillation amplitude of the oscillating unit when immersed in different media can thus be taken into account. The oscillating unit is thus subjected in each case to a signal having an appropriate amplitude, which is chosen in such a manner that the amplitude of the receiving signal is located within a specified, selectable interval.

In an additional advantageous embodiment, the electronics unit is designed to perform a frequency sweep to excite the oscillating unit, in the event that a specifiable lower threshold value for the amplitude is not reached, and to successively set the center frequency of the adaptive filter to consecutive, discrete excitation frequencies within a specifiable frequency interval. During operation, for example, as soon as the resonance frequency drops below a specifiable threshold value for the amplitude, a change from phase control to control of the sensor can be made via excitation by means of a frequency sweep. To do this, the center frequency of the adaptive filter is set to discrete consecutive frequencies within a specifiable frequency band. As soon as the threshold value for the amplitude is again exceeded (meaning, for example, that the oscillating unit again oscillates freely), it can be switched to the original mode, in which the excitation is accomplished via a target phase shift.

It is advantageous for the process variable to be a pre-determined fill-level, density, and/or viscosity of the medium in the container.

It is also advantageous for the oscillating unit to be a membrane, a rod, or a vibrating fork.

It is, furthermore, advantageous for the driving/receiving unit to be an electromagnetic or a piezoelectric driving/receiving unit.

The object of the invention is additionally achieved via a method for operating a vibronic sensor for determining and/or monitoring at least one process variable of a medium in a container—especially, according to at least one of the preceding claims—wherein a mechanical oscillating unit is excited to mechanical oscillations via an electric excitation signal, and the mechanical oscillations of the mechanical oscillating unit are received and transformed into an electric receiving signal, wherein the receiving signal is created on the basis of the receiving signal, and the at least one process variable is determined, and wherein the filter characteristics of the adaptive filter are set in such a manner that there is a target phase shift between the excitation signal and the receiving signal. The method according to the invention can also be used for digital as well as for analog versions of the oscillating circuit for exciting the oscillating unit. Likewise, by using the method according to the invention, different phase adjustment tolerances can be implemented, depending upon the application, and different target phase shifts can be set, depending upon the application.

It is advantageous for the center frequency of the adaptive filter to be controlled in such a manner that there is a target phase shift between the excitation signal and the receiving signal. This occurs by setting the phase shift $\phi_{filter}$ between the input signal and the output signal of the adaptive filter. This allows the determination of the oscillating frequency of the mechanical oscillating unit from the excitation, thus bringing a simplification with respect to signal evaluation within the electronics unit.

An additional preferred embodiment of the method includes setting the bandwidth of the adaptive filter. This means that the quality of the filter is set. A high bandwidth enables simple and quick detection of the resonant frequency of the oscillating unit, because the oscillating unit can be excited in this manner using frequencies within a large frequency range. If, however, no resonance is detected over the entire available frequency interval, it can be concluded, for example, that there is a blockage and/or a defect in the mechanical oscillating unit. By contrast, during the measurement operation, the bandwidth can be selected to be as small as possible, to eliminate the influence of interference signals and to correspondingly maximize the measurement precision as much as possible.

It is advantageous for 90°, 45°, or 0° to be set as the target phase shift. It is also advantageous for at least the first and the second target phase shifts to be alternately set.

Finally, it is also advantageous for the amplitude of the excitation signal to be set to a specifiable value or to a value within a specifiable interval. The amplitude dynamics can thus be controlled. The oscillating unit is thus subjected in each case to a signal having an appropriate amplitude, which is chosen in such a manner that the amplitude of the receiving signal is located within a specified, selectable interval.

BRIEF DESCRIPTION OF THE DRAWINGS

The invention, as well as its advantageous embodiments, are more closely described below with reference to FIG. 1 and FIG. 2. Illustrated are.

DETAILED DISCUSSION IN CONJUNCTION WITH THE DRAWINGS

Figure 1:
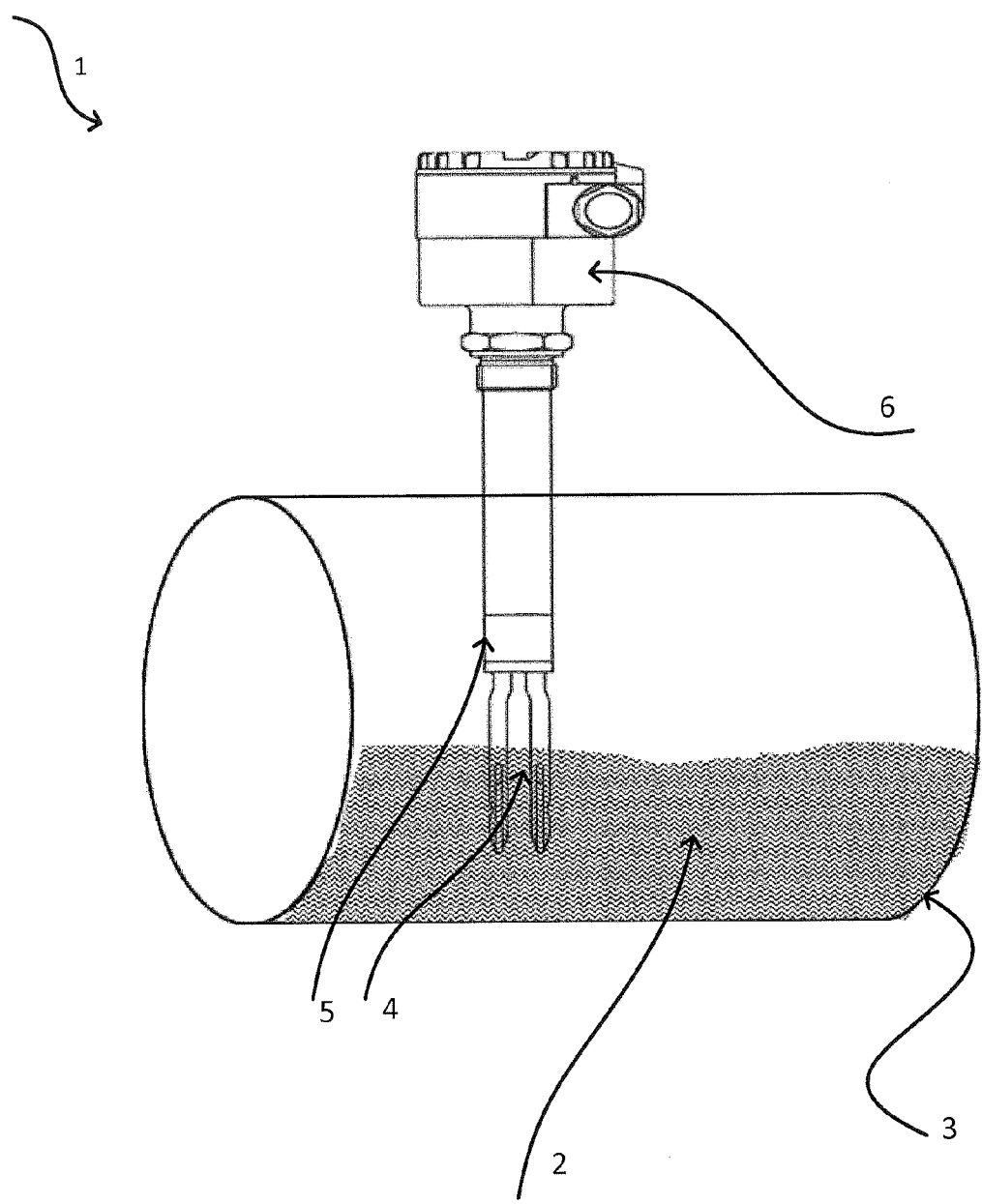
FIG. 1: a schematic drawing of a vibronic sensor according to the prior art.

A vibronic sensor 1 is shown in FIG. 1. A vibration-capable unit 4 is depicted in the form of an oscillating fork which is submerged partially into a medium 2, which is located in a container 3. The vibration-capable unit is stimulated by the triggering/receiving unit 5 to mechanical vibrations and can, for example, be a piezoelectric stack- or bi-morph actuator. However, it is naturally understood that other embodiments of a vibronic sensor also fall under the invention. In addition, an electronics unit 6 is illustrated, by means of which the signal reception, evaluation, and/or storage are accomplished.

Figure 2:
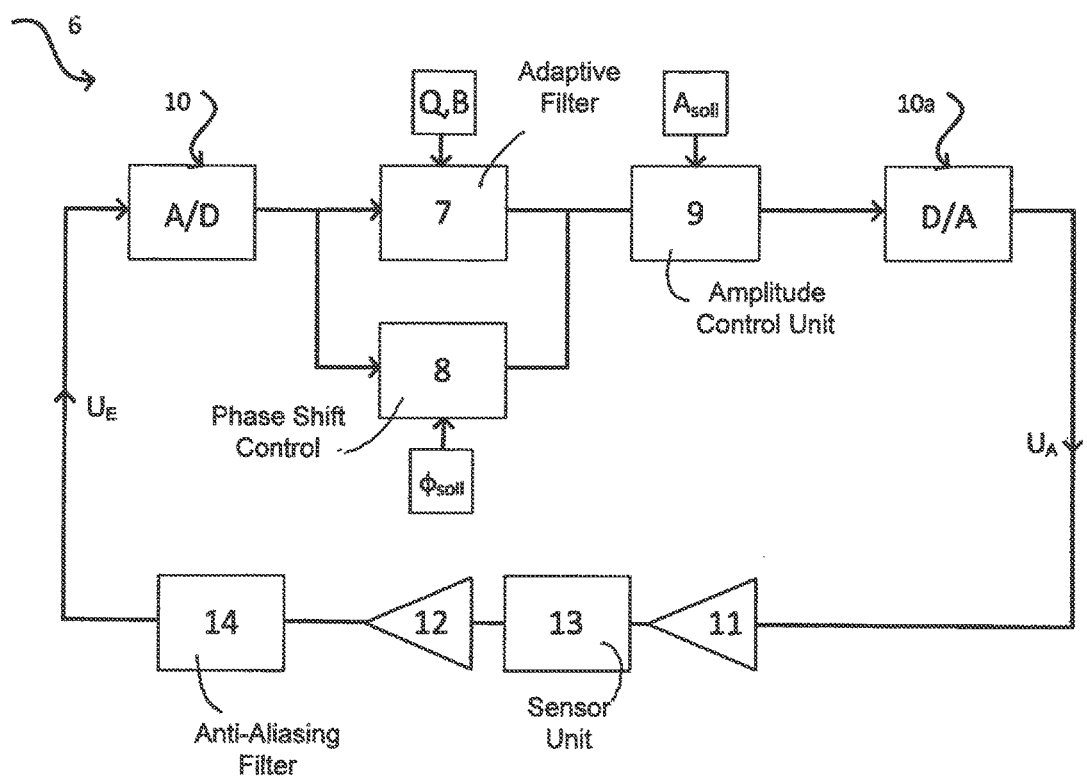
FIG. 2: a block diagram of an electronics unit according to the invention.

A block diagram of an electronics unit according to the invention is the subject of FIG. 2. The receiving signal $U_E$ first passes through an analog/digital converter 10 before it is supplied to the adaptive filter 7. The filter characteristics of the adaptive filter are set in such a manner that there is an appropriate phase shift $\phi_{filter}$ between the input signal and the output signal of the adaptive filter. This produces a target phase shift $\phi_{soll}=360°-\phi_{Filter}$ between the excitation signal and the receiving signal. A target phase shift can also be set between the excitation signal and the receiving signal via an appropriate adjustment of the filter characteristics. For example, a phase control unit 8 can be used that controls the center frequency $f_m$ of the adaptive filter in such a manner that there is a target phase shift $\phi_{soll}$ between the excitation signal and the receiving signal. Phase control unit 8, in turn, can be based upon the principle of a lock-in amplifier, for example.

The quality Q of adaptive filter 7 can be set by the so-called Lehr damping ratio D, among others. The following relationship can be used for this: Q=1/2 D, wherein the Lehr damping ratio, in turn, is determined from the mechanical properties of the oscillating unit.

Quality Q of adaptive filter 7 is additionally related via the relationship B=fm/Q to the quality Q and the center frequency of the adaptive filter $f_m$. An embodiment of the invention includes the ability to set quality Q of adaptive filter 7 or its bandwidth B.

Receiving signal $U_E$ is characterized by its frequency, its amplitude, and its phase. The phase control of phase control unit 8 is accomplished by setting center frequency $f_m$ of adaptive filter 7 to the input frequency of the adaptive filter, so that the frequency at which the oscillating unit oscillates is known at every instant.

Furthermore, according to a different embodiment, an amplitude control unit 9 can be integrated into electronics unit 6. By means of amplitude control unit 9, the amplitude A of the excitation signal $U_A$ comprises a specifiable value or a value within a specifiable interval. For example, a standard P1 controller can be used for this purpose.

An advantage of the invention is that, by using an adaptive filter 7 to excite mechanical oscillating unit 4, no additional filter is needed for filtering the signal prior to evaluation.

Before excitation signal $U_A$ is transmitted via output stage 11 of the electronics unit to sensor unit 13, it passes through a digital/analog converter 10a. Optionally, receiving signal $U_E$ received by sensor unit 13 can also be passed through an anti-aliasing filter 14 before it is further transmitted to analog/digital converter 10 after passing through input stage 12.

The invention claimed is:

1. A vibronic sensor for determining and/or monitoring at least one process variable of a medium in a container, comprising:
   at least one unit which can oscillate mechanically;
   a driving/receiving unit; and
   an electronics unit, wherein:

said driving/receiving unit is designed to excite, via an electrical excitation signal, mechanical oscillations in said at least one unit which can oscillate mechanically and to receive said mechanical oscillations of said at least one unit which can oscillate mechanically, and to convert said mechanical oscillations into an electrical receiving signal;

said electronics unit is designed to generate the excitation signal on the basis of said receiving signal and to determine said at least one process variable from the receiving signal;

said electronics unit comprises at least one adaptive filter;

said electronics unit is designed to set a filter characteristic of said adaptive filter in such a way that there is a target phase shift between said excitation signal and said receiving signal;

said electronics unit is designed to set said target phase shift by setting a center frequency of said adaptive filter; and said electronics unit comprises a phase control unit, which controls said center frequency of said adaptive filter in such a manner that there is a specifiable value for a phase shift between an input signal and an output signal of said adaptive filter.

2. The vibronic sensor according to claim 1, wherein:
said electronics unit comprises a ring memory and/or a phase shifter, by which said target phase shift can be set.

3. The vibronic sensor according to claim 1, wherein:
a bandwidth of said adaptive filter is adjustable.

4. The vibronic sensor according to claim 1, wherein:
said adaptive filter is a resonator filter.

5. The vibronic sensor according to claim 1, wherein:
said adaptive filter is a band pass filter.

6. The vibronic sensor according to claim 1, wherein:
said phase control unit is based upon the principle of a lock-in amplifier.

7. The vibronic sensor according to claim 1, wherein:
said target phase shift is 90°, 45°, or 0°.

8. The vibronic sensor according to claim 1, wherein:
at least a first and a second target phase shift are alternately adjustable.

9. The vibronic sensor according to claim 1, wherein:
said electronics unit comprises an amplitude control unit for controlling an amplitude of the excitation signal to a specifiable value or to a value within a specifiable interval.

10. The vibronic sensor according to claim 1, wherein:
said electronics unit is designed to perform a frequency search to excite said at least one unit which can oscillate mechanically in the event that a specifiable lower threshold value for an amplitude is not reached and to successively set a center frequency of said adaptive filter to consecutive, discrete excitation frequencies within a specifiable frequency interval.

11. The vibronic sensor according to claim 1, wherein:
said process variable is a pre-determined fill level, density, and/or viscosity of said medium in said container.

12. The vibronic sensor according to claim 1, wherein:
said at least one unit which can oscillate mechanically is a membrane, a rod, or a vibrating fork.

13. The vibronic sensor according to claim 1, wherein:
said driving/receiving unit is an electromagnetic or a piezoelectric driving/receiving unit.

14. A method for operating a vibronic sensor for determining and/or monitoring at least one process variable of a medium in a container, comprising:

exciting a mechanical oscillating unit to mechanical oscillations via an electrical excitation signal;

receiving said mechanical oscillations of said mechanical oscillating unit;

converting said mechanical oscillations of said mechanical oscillating unit into an electrical receiving signal;

creating said excitation signal originating from said receiving signal; and determining said at least one process variable, wherein:

a filter characteristics of an adaptive filter comprised in an electronics unit of said vibronic sensor are determined in such a manner that there is a target phase shift between said excitation signal and said receiving signal;

a center frequency of the adaptive filter is controlled in such a manner that there is a target phase shift between the excitation signal and the receiving signal; and said center frequency of said adaptive filter is controlled by a phase control unit comprised in said electronics unit is such a manner that there is a specifiable value for a phase shift between an input signal and an output signal of said adaptive filter.

15. The method according to claim 14, wherein:
a bandwidth of the adaptive filter is determined.

16. The method according to claim 14, wherein:
the target phase shift is set at 90°, 45°, or 0°.

17. The method according to claim 14, wherein:
at least a first and a second target phase shift are alternately set.

18. The method according to claim 14, wherein:
an amplitude of the excitation signal is set to a specifiable value or to a value within a specifiable interval.

* * * * *